(12) United States Patent
Wellwood et al.

(10) Patent No.: US 8,957,340 B2
(45) Date of Patent: Feb. 17, 2015

(54) SORTING MINED MATERIAL

(75) Inventors: Grant Ashley Wellwood, Pheasant Creek (AU); Samuel Kingman, Burton on Trent (GB)

(73) Assignee: Technological Resources Pty Ltd, Melbourne, Victoria (AU)

( * ) Notice: Subject to any disclaimer, the term of this patent is extended or adjusted under 35 U.S.C. 154(b) by 0 days.

(21) Appl. No.: 13/643,692

(22) PCT Filed: Apr. 28, 2011

(86) PCT No.: PCT/AU2011/000479
§ 371 (c)(1),
(2), (4) Date: Jan. 3, 2013

(87) PCT Pub. No.: WO2011/134009
PCT Pub. Date: Nov. 3, 2011

(65) Prior Publication Data
US 2013/0098807 A1    Apr. 25, 2013

(30) Foreign Application Priority Data

Apr. 28, 2010    (AU) ................................ 2010901791

(51) Int. Cl.
*B07C 5/00*    (2006.01)
*B07B 13/00*   (2006.01)
*G01N 23/083*  (2006.01)
*G01N 23/12*   (2006.01)

(52) U.S. Cl.
CPC ............ *B07B 13/003* (2013.01); *G01N 23/083* (2013.01); *G01N 23/12* (2013.01)
USPC ........................... 209/576; 209/577; 209/588

(58) Field of Classification Search
USPC ............ 209/576, 552, 11, 3.1, 639, 587, 571, 209/582, 577, 588
See application file for complete search history.

(56) References Cited

U.S. PATENT DOCUMENTS

| | | | | |
|---|---|---|---|---|
| 3,701,419 | A | | 10/1972 | Hutter et al. |
| 4,212,397 | A | * | 7/1980 | Bockelmann ................... 378/47 |
| 5,209,355 | A | * | 5/1993 | Mindermann ................. 209/3.1 |
| 5,695,039 | A | * | 12/1997 | Driscoll et al. ............... 194/212 |

(Continued)

FOREIGN PATENT DOCUMENTS

| | | |
|---|---|---|
| GB | 2198242 A | 6/1988 |
| JP | 61110016 A  * | 5/1986 |
| WO | WO 2007/051225 A1 | 5/2007 |

OTHER PUBLICATIONS

International Search Report issued by the Australian Patent Office in International Application No. PCT/AU2011/000479, mailed Jul. 22, 2011 (2 pages).

(Continued)

*Primary Examiner* — Luis A Gonzalez
(74) *Attorney, Agent, or Firm* — Banner & Witcoff, Ltd.

(57) ABSTRACT

A method and an apparatus for sorting mined material, such as mined ore, are disclosed. The apparatus comprises a chamber for exposing fragments of a material to be sorted to electromagnetic radiation, with the chamber comprising an inner wall for fragments to move downwardly and outwardly over from an upper inlet of the chamber to a lower outlet of the chamber. The apparatus also comprises a detection system for assessing one or more than one characteristic of the fragments. The apparatus also comprises a sorting means for separating the fragments into multiple streams in response to the assessment of the detection system.

18 Claims, 1 Drawing Sheet

(56) References Cited

U.S. PATENT DOCUMENTS

| | | | |
|---|---|---|---|
| 6,265,683 B1* | 7/2001 | Flottmann et al. | 209/576 |
| 8,307,985 B2* | 11/2012 | Dufresne et al. | 209/11 |
| 8,443,980 B2* | 5/2013 | Harding et al. | 209/4 |
| 2010/0204825 A1* | 8/2010 | Morrison | 700/223 |
| 2011/0180638 A1* | 7/2011 | Harding et al. | 241/24.1 |

OTHER PUBLICATIONS

International Preliminary Report on Patentability issued by the Australian Patent Office in International Application No. PCT/AU2011/000479, dated Mar. 6, 2012 (5 pages).

* cited by examiner

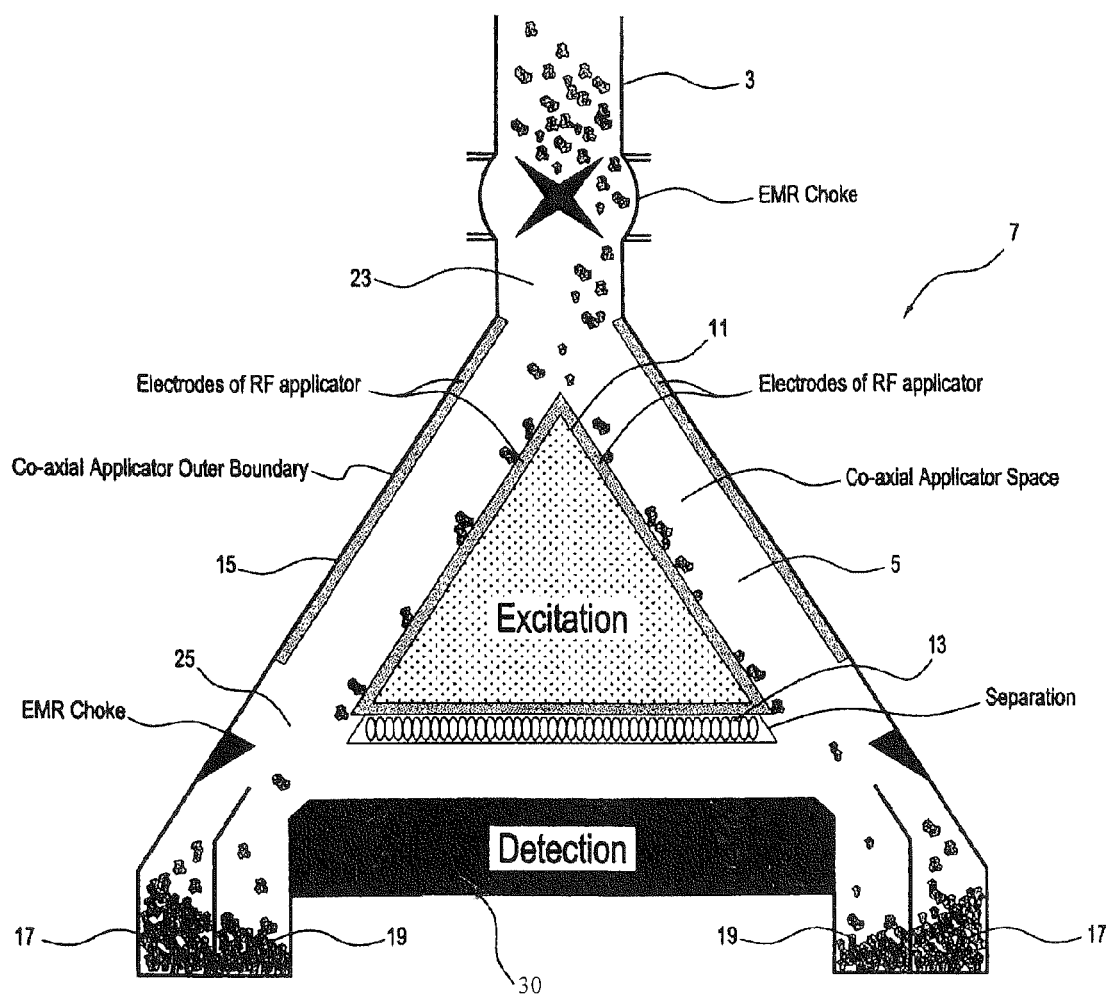

SORTING MINED MATERIAL

CROSS REFERENCE TO RELATED APPLICATIONS

This application is a national phase application based on PCT/AU2011/000479, filed Apr. 28, 2011, which claims priority of Australian Patent Application No. 2010901791, filed Apr. 28, 2010, the contents of all of which are incorporated herein by reference.

The present invention relates to a method and an apparatus for sorting mined material.

The present invention relates particularly, although by no means exclusively, to a method and an apparatus for sorting mined material for subsequent processing to recover valuable material, such as valuable metals, from the mined material.

The present invention also relates to a method and an apparatus for recovering valuable material, such as valuable metals, from mined material that has been sorted as described above.

The present invention relates to the use of electromagnetic radiation to cause a change in a fragment of a mined material that provides information on characteristics of the mined material in the fragment that is helpful for sorting and/or downstream processing of the fragment and that can be detected by one or more than one sensor. The information may include any one or more of the characteristics of composition, hardness, porosity, structural integrity, and texture of the fragment.

The present invention relates particularly, although by no means exclusively, to a method and an apparatus for sorting low grade mined material at high throughputs.

The invention is not confined to any particular type of electromagnetic radiation. The current focus of the applicant is in the microwave energy band of the electromagnetic radiation spectrum. However, radio frequency radiation and x-ray radiation are two other options amongst the range of options in the electromagnetic radiation spectrum that are of interest to the applicant and have been the subject of work by the applicant.

The mined material may be any mined material that contains valuable material, such as valuable metals. Examples of valuable materials are valuable metals in minerals such as minerals that comprise metal oxides or metal sulphides. Specific examples of valuable materials that contain metal oxides are iron ores and nickel laterites. Specific examples of valuable materials that contain metal sulphides are copper-containing ores. Another example of a valuable material is salt.

The term "mined" material is understood herein to include, but is not limited to, (a) run-of-mine material and (b) run-of-mine material that has been subjected to at least primary crushing or similar size reduction after the material has been mined and prior to being sorted. The mined material includes mined material that is in stockpiles.

A particular area of interest to the applicant is mined material in the form of mined ores that include copper-containing minerals such as chalcopyrite, in sulphide forms.

The present invention is particularly, although not exclusively, applicable to sorting low grade mined material.

The term "low" grade is understood herein to mean that the economic value of the valuable material, such as a metal, in the mined material is only marginally greater than the costs to mine and recover and transport the valuable material to a customer.

In any given situation, the concentrations that are regarded as "low" grade will depend on the economic value of the valuable material and the mining and other costs to recover the valuable material from the mined material at a particular point in time. The concentration of the valuable material may be relatively high and still be regarded as "low" grade. This is the case with iron ores.

In the case of valuable material in the form of copper sulphide minerals, currently "low" grade ores are run-of-mine ores containing less than 1.0% by weight, typically less than 0.6 wt. %, copper in the ores. Sorting fragments of valuable material from barren fragments in ores having such low concentrations of copper is a challenging task from a technical viewpoint, particularly in situations where there is a need to sort very large amounts of ore, typically at least 10,000 tonnes per hour, and where the barren fragments represent a smaller proportion of the ore than the ore that contains economically recoverable copper.

The term "barren" fragments when used in the context of copper-containing ores are understood herein to mean fragments with no copper or very small amounts of copper that can not be recovered economically from the fragments.

The term "barren" fragments when used in a more general sense in the context of valuable materials is understood herein to mean fragments with no valuable material or amounts of valuable material that can not be recovered economically from the fragments.

The applicant is developing an automated sorting apparatus to process mined material in the form of low grade copper-containing ores. In general terms, processing such a feed ore comprises the following discrete steps:
  (a) exciting target minerals within a feed ore,
  (b) identifying ore fragments based on mineral composition or texture or other characteristic, and
  (c) physical separation of targeted fragments.

Automated ore sorting apparatus known to the applicant has been limited to low throughput, high grade and/or self identification systems. The general approach used in these low throughput sorting systems is to convey ore fragments through the apparatus on a horizontal belt.

An issue for the technology development path of the applicant relates to detecting mineralisation at low concentrations and in high throughputs. Detection of low concentrations of mineralisation can be addressed by selectively exciting target minerals using electromagnetic radiation. However, this approach requires the use of an "applicator" (where the electromagnetic radiation can be applied to the fragments in a controlled manner). Generally, applicators are a separate device that complicates the sorting apparatus and sorting methods.

The above description is not to be understood as an admission of the common general knowledge in Australia or elsewhere.

According to the present invention there is provided an apparatus for sorting mined material, such as mined ore, that comprises:
  (a) a chamber for exposing fragments of a material to be sorted to electromagnetic radiation, with the chamber comprising an inner wall for fragments to move downwardly and outwardly over from an upper inlet of the chamber to a lower outlet of the chamber,
  (b) a detection system for assessing one or more than one characteristic of the fragments after the fragments have been exposed to electromagnetic radiation, and
  (c) a sorting means for separating the fragments into multiple sorted streams in response to the assessment of the detection system.

In use, fragments of a feed ore are supplied to the upper inlet of the exposure chamber and slide, tumble, or otherwise move down the inner wall of the chamber. The feed ore fragments are exposed to electromagnetic radiation as they move down the inner wall. The inner wall distributes the feed ore fragments downwardly and outwardly from the upper inlet over the surface of the inner wall. A downwardly-falling curtain of the feed ore fragments are discharged from the lower outlet of the exposure chamber. The detection system assesses one or more than one characteristic of the feed ore fragments in the curtain of fragments. The sorting means sorts the feed ore fragments based on the assessment. This arrangement makes it possible to process feed ore at a high throughput and the curtain of feed ore fragments is a convenient form for high throughput analysis and then separation of the fragments.

The term "fragment" is understood herein to mean any suitable size of mined material having regard to materials handling and processing capabilities of the apparatus used to carry out the method and issues associated with detecting sufficient information to make an accurate assessment of the mined material in the fragment.

The exposure chamber may be formed so that the fragments move downwardly and outwardly through the chamber as separate fragments.

The exposure chamber may be adapted to discharge the fragments from the lower outlet as a downwardly-falling curtain in which the fragments in the curtain move as separate fragments.

The inner wall of the exposure chamber may be an inverted inner conical surface.

The inner conical surface may define any suitable angle to a horizontal axis.

The inner conical surface may define an angle of at least 30° to a horizontal axis.

The inner conical surface may define an angle of at least 45° to a horizontal axis.

The inner conical surface may define an angle of less than 75° to a horizontal axis.

The inner wall of the exposure chamber may be an angled plate.

The plate may be a flat plate.

The angle of the flat plate may be any suitable angle to a horizontal axis.

The exposure chamber may comprise an outer wall that is spaced outwardly from the inner wall.

In the case of an arrangement in which the inner wall of the exposure chamber is an inverted inner conical surface, the outer wall of the exposure chamber may have an inverted outer conical surface that is co-axial with the inner conical surface so that the exposure chamber defines a conical annular space between the inner and the outer walls.

The electromagnetic radiation used in the exposure chamber may be any suitable radiation. For example, the radiation may be X-ray, microwave and radio frequency radiation.

The electromagnetic radiation may be pulsed or continuous electromagnetic radiation.

The selection of exposure parameters, such as the type of radiation and the length of exposure and the energy of the radiation, in the exposure chamber may be based on known information on the mined material and downstream processing options for the mined material.

The detection system may comprise a sensor for detecting the response, such as the thermal response, of each fragment to electromagnetic radiation.

The detection system may comprise at least another sensor for detecting another characteristic of the fragment. Other characteristics may include any one or more of hardness, texture, structural integrity, and porosity of the fragments.

The detection system may comprise a processor for analysing the sensed data for each fragment, for example using an algorithm that takes into account the sensed data, and classifying the fragment for sorting and/or downstream processing of the fragment, such as heap leaching and smelting.

The assessment of the fragments may be on the basis of grade of a valuable metal in the fragments. The assessment of the fragments may be on the basis of another characteristic (which could also be described as a property), such as any one or more of hardness, texture, structural integrity, and porosity of the fragments. In general terms, the purpose of the assessment of the fragments is to facilitate sorting of the fragments and/or downstream processing of the fragments.

The apparatus may be adapted to sort mined material at any suitable throughput. The required throughput in any given situation is dependent on a range of factors including, but not limited to, operating requirements of upstream and downstream operations.

The apparatus may be adapted to sort at least 100 tonnes per hour of mined material.

The apparatus may be adapted to sort at least 500 tonnes per hour of mined material.

The mined material may be a copper-containing ore.

The copper-containing ore may be a low grade ore.

The copper-containing ore may contain chalcopyrite.

According to the present invention there is provided a method of sorting mined material, such as mined ore, comprising the steps of:
  (a) exposing individual fragments of the mined material to electromagnetic radiation as the fragments move downwardly and outwardly through an exposure chamber of an apparatus for sorting mined material from an upper inlet of the chamber to a lower outlet of the chamber;
  (b) detecting one or more than one characteristic of the fragments,
  (c) assessing the characteristic(s) of the fragments, and
  (d) sorting the fragments into multiple streams in response to the assessment of the detection system.

Step (a) may comprise moving the fragments downwardly and outwardly through the exposure chamber as separate fragments and exposing the fragments to electromagnetic radiation as the fragments move through the exposure chamber.

Step (b) may comprise detecting the response, such as the thermal response, of each fragment to exposure to electromagnetic radiation.

Step (b) is not confined to detecting the response of fragments of the mined material to electromagnetic radiation and extends to detecting additional characteristics of the fragments. For example, step (b) extends to the use of any one or more than one of the following sensors to detect characteristics of the mined material: (i) near-infrared spectroscopy ("NIR") sensors, (ii) optical sensors, (iii) acoustic wave sensors (for internal structure for leach and grind dimensions), (iv) laser induced spectroscopy ("LIBS") sensors, and (v) magnetic property sensors.

Step (c) may comprise assessing the response of each fragment to exposure to electromagnetic radiation to identify valuable material in the fragment.

The method may comprise a downstream processing step of comminuting the sorted material from step (d) as a pre-treatment step of recovering the valuable mineral from the mined material.

The method may comprise a downstream processing step of blending the sorted material from step (d) as a pre-treatment step of recovering the valuable mineral from the mined material.

The method may comprise using the sensed data for each fragment as feed-forward information for downstream processing options, such as flotation and comminution, and as feed-back information to upstream mining and processing options.

The method may comprise upstream mining and processing options.

The upstream mining and processing options may include a pre-sorting step.

The upstream mining and processing options may include drill and blast operations, the location of mining operations, and crushing operations.

The method may comprise sorting at least 100 tonnes per hour of mined material.

The method may comprise sorting at least 500 tonnes per hour of mined material.

According to the present invention there is also provided a method for recovering valuable material, such as a valuable metal, from mined material, such as mined ore, that comprises sorting mined material according to the method described above and thereafter processing the fragments containing valuable material and recovering valuable material.

The method may comprise sorting at least 100 tonnes per hour of mined material.

The method may comprise sorting at least 500 tonnes per hour of mined material.

The processing options for the sorted fragments may be any suitable options, such as smelting and leaching options.

The present invention is described further by way of example with reference to the accompanying drawing which illustrates diagrammatically a vertical cross-section of one embodiment of key components of a sorting apparatus in accordance with the present invention.

The embodiment is described in the context of a method and an apparatus for recovering a valuable metal in the form of copper from a low grade copper-containing ore in which the copper is present in copper-containing minerals such as chalcopyrite and the ore also contains non-valuable gangue. The objective of the method in this embodiment is to identify fragments of mined material containing amounts of copper-containing minerals above a certain grade and to sort these fragments from the other fragments and to process the copper-containing fragments as required to recover copper from the fragments.

It is noted that, whilst the following description does not focus on the downstream processing options, these options are any suitable options ranging from smelting to leaching the fragments.

It is also noted that the present invention is not confined to copper-containing ores and to copper as the valuable material to be recovered. In general terms, the present invention provides a method of sorting any minerals which exhibit different heating responses when exposed to electromagnetic radiation.

It is also noted that the term "fragment" as used herein may be understood by some persons skilled in the art to be better described as "particles". The intention is to use both terms as synonyms.

With reference to the drawing, a feed material in the form of fragments of copper-containing ore that have been crushed by a primary crusher (not shown) to a fragment size of 10-25 cm is supplied via a downwardly extending transfer chute 3 (or other suitable transfer means) to a microwave radiation treatment station generally identified by the numeral 7 and described further below and is exposed to microwave radiation on a fragment by fragment basis as the fragments move downwardly through a frusto-conical annular exposure chamber 5 of the treatment station 7.

While passing through the exposure chamber 5, radiation emitted from the fragments, as a consequence of (a) exposure to microwave energy and (b) the characteristics (such as composition and texture) of the fragments, is detected by high resolution, high speed infrared imagers (not shown) which capture thermal images of the fragments. This detection system is depicted generally by "Detection" 30 of the FIGURE. While one thermal imager is sufficient, two or more thermal imagers may be used for full coverage of the fragment surface. It is noted that the present invention is not limited to the use of such high resolution, high speed infrared imagers. It is also noted that the present invention is not limited to detecting the thermal response of fragments to microwave energy and extends to detecting other types of response.

In addition, one or more visible light cameras (not shown) capture visible light images of the fragments to allow determination of fragment size. Depicted generally by "Detection" 30 of the FIGURE.

The present invention also extends to the use of other detectors for detecting other characteristics of the fragments, such as texture. Depicted generally by "Detection" 30 of the FIGURE.

From the number of detected hot spots (pixels), temperature, pattern of their distribution and their cumulative area, relative to the size of the fragment, an estimation of the grade of observed rock fragments can be made. This estimation may be supported and/or more mineral content may be quantified by comparison of the data with previously established relationships between microwave induced thermal properties of specifically graded and sized rock fragments.

Images collected by the thermal imagers and the visible light cameras are processed using a computer (not shown) equipped with image processing and other relevant software. The software is designed to process the sensed data from the thermal imagers and the visible light cameras to assess the fragments for sorting and/or downstream processing options. In any given situation, the software may be designed to weight different data depending on the relative importance of the properties associated with the data. Once the thermal and visual light analysis is completed by the computer and each fragment is assessed, the fragments are separated into one of two (or possibly more) categories.

The fragments free-fall from the exposure chamber 5 and are separated into annular collection bins 17, 19 by means of compressed air jets (or other suitable fluid jets, such as water jets, or any suitable mechanical devices, such as mechanical flippers) that selectively deflect the fragments as the fragments move in a free-fall trajectory from a lower end of the exposure chamber 5. The air jet nozzles are identified by the numeral 13. The air jets selectively deflect the fragments into two circular curtains of fragments that free-fall into the collection bins 17, 19. The thermal analysis identifies the position of each of the fragments and the air jets are activated a pre-set time after a fragment is analysed as a fragment to be deflected.

The treatment station 7 comprises the above-mentioned frusto-conical exposure chamber 5. The exposure chamber 5 comprises an inner wall having an inverted inner conical surface 11 for particles to slide, tumble, or otherwise move downwardly and outwardly over from an upper central inlet 23 of the exposure chamber 5 to a lower annular outlet 25 of the exposure chamber 5. The inner conical surface 11 describes an angle α of 60° to a horizontal axis. The inner conical surface 11 is shrouded by an outer wall having a second concentric outer inverted conical surface 15. The annular exposure chamber 5 functions as an applicator. The arrangement is such that feed material that is supplied to the upper central inlet 23 slides, tumbles, or otherwise moves down the inner conical surface 11. The inner conical surface 11 distributes the fragments of the feed material downwardly and outwardly over the surface 11 so that the fragments are separated from each other and move as separate fragments. This is an effective arrangement for handling a high throughput of feed material and making it possible to process the material on a fragment by fragment basis.

The apparatus has a particular advantage in the case of electromagnetic radiation in the radio frequency band, where the inner conical surface 11 and the outer conical surface 15 are electrically isolated and configured to form parallel electrodes of a radio frequency applicator.

The microwave radiation may be either in the form of continuous or pulsed radiation.

The microwave radiation may be applied at a power density below that which is required to induce micro-fractures in the fragments. In any event, the microwave frequency and microwave intensity and the fragment exposure time and the other operating parameters of the microwave treatment station 7 are selected having regard to the information that is required.

The required information is information that is required to assess the particular mined material for sorting and/or downstream processing of the fragments. In any given situation, there will be particular combinations of characteristics, such as grade, mineralogy, hardness, texture, structural integrity, and porosity, that will provide the necessary information to make an informed decision about the sorting and/or downstream processing of the fragments, for example, the sorting criteria to suit a particular downstream processing option.

There may be a range of other sensors (not shown) other than thermal imagers and visible light cameras mentioned above positioned within and/or downstream of the microwave exposure chamber 5 to detect other characteristics of the fragments depending on the required information to classify the fragments for sorting and/or downstream processing options.

In one mode of operation the thermal analysis is based on distinguishing between fragments that are above and below a threshold temperature. The fragments can then be categorised as "hotter" and "colder" fragments. The temperature of a fragment is related to the amount of copper minerals in the fragment. Hence, fragments that have a given size range and are heated under given conditions will have a temperature increase to a temperature above a threshold temperature "x" degrees if the fragments contain at least "y" wt. % copper. The threshold temperature can be selected initially based on economic factors and adjusted as those factors change. Barren fragments will generally not be heated on exposure to radio frequency radiation to temperatures above the threshold temperature.

In the present instance, the primary classification criteria is the grade of the copper in the fragment, with fragments above a threshold grade being separated into collection bin 19 and fragments below the threshold grade being separated into the collection bin 17. The valuable fragments in bin 19 are then processed to recover copper from the fragments. For example, the valuable fragments in the bin 19 are transferred for downstream processing including milling and flotation to form a concentrate and then processing the concentrate to recover copper.

The fragments in collection bin 17 may become a byproduct waste stream and are disposed of in a suitable manner. This may not always be the case. The fragments have lower concentrations of copper minerals and may be sufficiently valuable for recovery. In that event the colder fragments may be transferred to a suitable recovery process, such as leaching.

Advantages of the present invention include the following advantages.

Fragment orientation changes during downward and outward movement of fragments in the exposure chamber 5 (many ores have orientation specific mineralisation within which can make them impervious to electromagnetic radiation. Belt based systems are characterised by fixed fragment orientation by fragments sliding down the inner cone will change orientation hence be less susceptible to orientation effects.

Dispersion. Higher solids loadings improve the operation of applicators. However, in conventional belt systems this is compromised by downstream requirements. To minimise separation errors the fragments need to be presented to the detection and separation units in a dispersed manner (typically one fragment diameter separation from an adjacent fragment.) In horizontal belt systems this creates intensity constraints as belt widths and speeds have limitations. In the present invention the fragments sliding, tumbling, or otherwise moving down the inner wall of the exposure chamber are continually accelerating so it is possible to have a high intensity at the top of the cone (good for electromagnetic radiation exposure) and a dispersed (horizontally by increasing diameter of cone and vertically by gravitational acceleration) distribution for the detection and separation stages.

Process intensity (tonnes/h/m$^2$ plan area). In order to be viable, high throughput sorters need high intensity. Unlike belt systems the present invention is capable of higher material throughput, at least 100 tonnes per hour, as it is unconstrained by mechanical issues like belt speed and loading. Most host sites are constrained by plan area availability hence vertical processing increases viability. The applicator and acceleration, presentation, detection, separation stages can be incorporated into a single device/space.

Mechanically and electromagnetically simpler. The present invention offers fewer moving parts overall and no moving parts in the applicator and simpler electromagnetic and mechanical design.

Economies of scale. The present invention could be scaled easily to very large size to create high capacity modules. Conventional belt based systems have virtually no economy of scale potential and there are practical limits on individual belt width as well.

Flexibility-staged processing. The temperature tag for sorting induced by electromagnetic radiation can be preserved for many seconds. The embodiment of a vertically orientated concentric cone is very amenable to stacking (cascade) and, hence, multiple detection separation stages which could employed using a single applicator to minimise sorting errors.

Containment: Dust, noise and electromagnetic radiation containment is made easier by the co-axial cone approach of the above-described embodiment where all the activity takes place in the annular space. This arrangement is also more conducive to environmental controls identified to enhance the process. Plug flow down the feed tube to the cone apex of the embodiment would function as an effective active choke in the case of electromagnetic radiation in the microwave frequencies.

Rotation of fragments sliding or tumbling or otherwise moving down the inner wall imparts twisting movement of fragments once the fragments go into free fall after being discharged from the exposure chamber. As the detection is normally done with the particles in free-fall, the cone approach of the embodiment and the twisting imparted may enhance the quality of this step by presenting more surfaces for inspection.

Many modifications may be made to the embodiment of the present invention described above without departing from the spirit and scope of the present invention.

For example, whilst the embodiment describes an exposure chamber 5 in the form of a conical annular space, the present invention is not so limited and extends to any arrangement that facilitates moving fragments downwardly and outwardly from an upper inlet 23 of the chamber 5. One such other arrangement is an angled plate.

By way of further example, whilst the embodiment includes a centrally located vertical transfer chute 3, the present invention is not so limited and extends to any arrangement that facilitates moving fragments to the upper inlet 23 of the exposure chamber 5.

The invention claimed is:

1. An apparatus for sorting mined material that comprises:
   (a) a chamber for exposing fragments of a material to be sorted to electromagnetic radiation, with the chamber comprising an inner wall angled at an acute angle to the horizontal for fragments to move downwardly and outwardly over the inner wall from an upper inlet of the chamber to a lower outlet of the chamber, wherein the inner wall comprises an inverted inner conical surface,
   (b) a detection system for assessing one or more than one characteristic of the fragments after the fragments have been exposed to electromagnetic radiation, and
   (c) a sorting means for separating the fragments into multiple sorted streams in response to the assessment of the detection system.

2. The apparatus defined in claim 1 wherein the exposure chamber is formed so that the fragments can move downwardly and outwardly through the chamber as separate fragments.

3. The apparatus defined in claim 1 wherein the exposure chamber comprises an outer wall that is spaced outwardly from the inner wall.

4. The apparatus defined in claim 3 wherein the outer wall of the exposure chamber comprises an inverted outer conical surface that is co-axial with the inner conical surface so that the exposure chamber defines a conical annular space between the inner and the outer walls.

5. The apparatus defined in claim 1 wherein the detection system comprises a sensor for detecting the response of each fragment to electromagnetic radiation.

6. The apparatus defined in claim 5 wherein the sensor is adapted to detect the thermal response of each fragment to electromagnetic radiation.

7. The apparatus defined in claim 6 wherein the detection system comprises at least one other sensor for detecting another characteristic of the fragment, including any one or more of hardness, texture, structural integrity, and porosity of the fragments.

8. The apparatus defined in claim 5 wherein the detection system comprises a processor for analysing the sensed data for each fragment and classifying the fragment for sorting and/or downstream processing of the fragment.

9. The apparatus defined in claim 1 wherein the apparatus is adapted to sort at least 100 tonnes per hour of mined material.

10. A method of sorting mined material comprising the steps of:
    (a) exposing individual fragments of mined material to electromagnetic radiation as the fragments move downwardly and outwardly at an acute angle to the horizontal over an inverted conical surface of an exposure chamber of an apparatus for sorting mined material from an upper inlet of the chamber to a lower outlet of the chamber;
    (b) detecting one or more than one characteristic of the fragments,
    (c) assessing the characteristic(s) of the fragments, and
    (d) sorting the fragments into multiple streams in response to the assessment of the detection system.

11. The method defined in claim 10 wherein step (a) comprises moving the fragments downwardly and outwardly through the exposure chamber as separate fragments and exposing the fragments to electromagnetic radiation as the separate fragments and exposing the fragments to electromagnetic radiation as the fragments move through the exposure chamber.

12. The method defined in claim 10 wherein step (b) comprises detecting the thermal response of each fragment to exposure to electromagnetic radiation.

13. The method defined in claim 10 wherein step (c) comprises assessing the response of each fragment to exposure to electromagnetic radiation to identify valuable material in the fragment.

14. The method defined in claim 10 comprising using the detected data for each fragment as feed-forward information for downstream processing options and as feed-back information to upstream mining and processing options.

15. The method defined in claim 10 comprising sorting at least 100 tonnes per hour of mined material.

16. The method defined in claim 10 comprising sorting at least 500 tonnes per hour of mined material.

17. A method for recovering valuable material from mined material that comprises sorting mined material according to the method defined in claim 15 and thereafter processing the fragments containing valuable material and recovering valuable material.

18. The method defined in claim 17 wherein the processing options for the sorted fragments comprise smelting and leaching options.

* * * * *